(12) United States Patent
Chen et al.

(10) Patent No.: US 11,444,056 B2
(45) Date of Patent: Sep. 13, 2022

(54) SANDWICH ASSEMBLY SCHEME FOR THIN FILM ELECTRODE ARRAY AND INTEGRATED CIRCUITS ON BOTH SIDES OF PRINTED CIRCUIT BOARD (PCB) AND METHOD OF MANUFACTURE

(71) Applicant: Neuralink Corp., Fremont, CA (US)

(72) Inventors: Supin Chen, San Ramon, CA (US); Camilo A. Diaz-Botia, Monte Sereno, CA (US); Dongjin Seo, San Francisco, CA (US); Vanessa M. Tolosa, Emeryville, CA (US)

(73) Assignee: Neuralink Corp., Fremont, CA (US)

( * ) Notice: Subject to any disclaimer, the term of this patent is extended or adjusted under 35 U.S.C. 154(b) by 0 days.

(21) Appl. No.: 16/924,495

(22) Filed: Jul. 9, 2020

(65) Prior Publication Data

US 2021/0008364 A1    Jan. 14, 2021

Related U.S. Application Data

(60) Provisional application No. 62/873,497, filed on Jul. 12, 2019.

(51) Int. Cl.
*A61N 1/04* (2006.01)
*H01L 23/00* (2006.01)
(Continued)

(52) U.S. Cl.
CPC ............ *H01L 24/97* (2013.01); *A61N 1/0529* (2013.01); *G01N 27/26* (2013.01); *A61B 2562/164* (2013.01); *H01L 23/481* (2013.01)

(58) Field of Classification Search
CPC .............................. H01L 24/97; G01N 27/26
See application file for complete search history.

(56) References Cited

U.S. PATENT DOCUMENTS

| 5,133,495 A | 7/1992 | Angulas et al. |
| 7,021,521 B2 * | 4/2006 | Sakurai ............... H01L 24/11 |
| | | 228/180.5 |

(Continued)

FOREIGN PATENT DOCUMENTS

WO    2017199052 A2    11/2017

OTHER PUBLICATIONS

Chung et al., A Polymer Probe-Based System for High Density, Long-Lasting Electrophysiological Recordings Across Distributed Neuronal Circuits, http://dx.doi.org/10.1101/242693, Jan. 4, 2018.
(Continued)

*Primary Examiner* — Ali Naraghi
(74) *Attorney, Agent, or Firm* — Kilpatrick Townsend & Stockton LLP (57) ABSTRACT

Disclosed is a sandwich assembly containing a thin film electrode array for use with high density electrodes. To minimize the volume required by the associated electronics, the electrode array and integrated circuits are sandwiched over a Printed Circuit Board (PCB), which may have other integrated circuits on an opposite side. Among other things, the disclosed apparatus, system, and method improve over previous systems by providing holes and vias that facilitate communication between a custom chip above the PCB and a field-programmable gate array (FPGA) below. The thin film electrode array can be fastened by bucking a pillar of stacked gold or other metal balls to rivet the thin film flex circuit. The system can include a thin film array having embedded wire traces and holes, a PCB having vias aligned with the holes, chips including an analog-to-digital converter (ADC) sandwiching the thin film, and solder connections from the chips through the holes to the vias.

25 Claims, 9 Drawing Sheets

(51) Int. Cl.
*A61N 1/05* (2006.01)
*G01N 27/26* (2006.01)
*H01L 23/48* (2006.01)

(56) References Cited

U.S. PATENT DOCUMENTS

| | | | |
|---|---|---|---|
| 7,226,821 B2 | 6/2007 | Primavera et al. | |
| 8,310,259 B2 * | 11/2012 | Hamel | G01R 31/2889 |
| | | | 324/756.03 |
| 8,618,795 B1 * | 12/2013 | Nagarkar | G01R 33/093 |
| | | | 324/228 |
| 8,707,734 B2 | 4/2014 | Haque et al. | |
| 9,420,953 B2 | 8/2016 | Litt et al. | |
| 9,437,566 B2 * | 9/2016 | Katkar | H01L 24/03 |
| 9,486,641 B2 * | 11/2016 | Tolosa | A61N 5/0622 |
| 9,949,051 B2 * | 4/2018 | Higgins | H04R 19/04 |
| 10,636,775 B2 * | 4/2020 | Chen | H01L 25/50 |
| 10,926,133 B2 * | 2/2021 | Giedwoyn | G16H 40/67 |
| 2008/0157353 A1 * | 7/2008 | Watanabe | H05K 3/3436 |
| | | | 257/734 |
| 2008/0178677 A1 * | 7/2008 | Baumgartner | B06B 1/0629 |
| | | | 73/606 |
| 2011/0237921 A1 * | 9/2011 | Askin, III | A61B 5/24 |
| | | | 607/116 |
| 2015/0305643 A1 * | 10/2015 | Negi | A61B 5/6846 |
| | | | 29/854 |
| 2020/0085375 A1 | 3/2020 | Tolosa et al. | |
| 2020/0086111 A1 | 3/2020 | Young et al. | |

OTHER PUBLICATIONS

P. Merz et al., A Novel Micromachining Technology for Structuring Borosilicate Glass Substrates, Transducers '03, pp. 258-261, Fraunhofer Institute for Silicon Technology (FHG ISIT), Itzehoe, Germany.

A. Tooker et al., "Towards a Large-Scale Recording System: Demonstration of Polymer-Based Penetrating Array for Chronic Neural Recording," 36$^{th}$ Annual International Conference of the IEEE Engineering in Medicine and Biology Society, Aug. 2014, LLNL-CONF-655518, Chicago, IL.

Application No. PCT/US2020/041345, International Search Report and Written Opinion, dated Dec. 10, 2020, 10 pages.

PCT/US2020/041345, International Preliminary Report on Patentability, dated Jan. 27, 2022, 7 pages.

* cited by examiner

SANDWICH ASSEMBLY SCHEME FOR THIN FILM ELECTRODE ARRAY AND INTEGRATED CIRCUITS ON BOTH SIDES OF PRINTED CIRCUIT BOARD (PCB) AND METHOD OF MANUFACTURE

CROSS-REFERENCES TO RELATED APPLICATIONS

This application claims the benefit of U.S. Provisional Patent Application No. 62/873,497, filed Jul. 12, 2019, which is hereby incorporated by reference in its entirety for all purposes.

STATEMENT AS TO RIGHTS TO INVENTIONS MADE UNDER FEDERALLY SPONSORED RESEARCH AND DEVELOPMENT

NOT APPLICABLE

BACKGROUND

1. Field of the Invention

Embodiments of the present invention generally relate to interconnections structures between semiconductor integrated circuit (IC) chips and multilayer flexible insulating substrates. More specifically, embodiments relate to apparatuses and processes for space-saving assemblies of biocompatible flexible substrate electrodes and printed circuit boards and IC chips.

2. Description of the Related Art

Implantable devices can be implanted into neurological tissue, such as the brain, to form a brain-computer interface. In certain instances, the implantable devices can contain a biocompatible substrate with conduits such as electrodes for stimulation of neurons (such as light, current, voltage, or drugs) and/or recording neuronal signals.

Such neuronal signals may be faint, analog, unprocessed signals, and may require analog-to-digital conversion, aggregation, and conversion to data packets and/or to human- or machine-readable formats, before they can be processed by digital computers. Such conversion, pre-processing, and formatting may require electronics occupying significant volume and adding significant weight to the brain implant. Accordingly, to make brain-computer interfaces viable, a lightweight, compact electronics package is needed.

There is a general need in the art for more compact electronics and interfaces between integrated circuits and stimulants from the outside world.

BRIEF SUMMARY

Generally, a ribbon cable of microfabricated thin film electrode connection wires are sandwiched between the body of an analog-to-digital converter (ADC) integrated circuit (IC) chip and a printed circuit board. Some of the electrode wires connect to a first row of pins on a first side of the ADC chip, and after the ribbon cable progresses underneath the ADC, other electrode wires connect to a second row of the ADC's pins. The output, digital pins of the ADC pass through a hole in the ribbon cable to the printed circuit board underneath and/or another IC chip mounted on an opposite side of the printed circuit board.

The ADC integrated circuit chip may also house a digital-to-analog converter (DAC) such that the ADC and DAC dual functions are on one chip, and the output, digital pins of the ADC serve as the input, digital pins of the DAC.

The present disclosure is related to a thin film electrode converter apparatus including a thin film having embedded wire traces, the wire traces leading from electrodes at a distal end of the thin film to a two-dimensional (2D) array of conductive pads, wherein some of the wire traces connect with a first row of the conductive pads and other of the wire traces connect with a second row of the conductive pads, the second row being farther from the distal end than the first row, the thin film having a hole through the thin film. The apparatus include a printed circuit board (PCB) having a via aligned with the hole through the thin film, an analog-to-digital converter (ADC) sandwiching the thin film between the ADC and the PCB and having ADC inputs electrically connected with at least one of the first and second rows of conductive pads of the thin film, and a solder connection running from an output of the ADC through the thin film hole to the PCB via.

In a further embodiment, the thin film electrode converter apparatus further includes an integrated circuit chip attached to a side of the PCB opposite the thin film and ADC, the integrated circuit chip connected with the PCB via.

In a further embodiment, the integrated circuit chip comprises a field programmable gate array (FPGA).

In a further embodiment, the ADC is configured to convert analog signals from multiple electrodes into digital signals and multiplex them together, the solder connection being configured to route the multiplexed digital signal from the ADC on one side of the thin film to the integrated circuit chip on another side, and the integrated circuit chip is configured to convert the multiplexed digital signals to a serialized data structure.

In a further embodiment, the serialized data structure is in a format selected from the group consisting of Protocol Buffers, Avro, Thrift, Bond, and extensible markup language (XML).

In a further embodiment, the ADC is configured to multiplex multiple digital signals together.

In a further embodiment, each conductive pad of the thin film is at least 5 times wider than its respective wire trace.

In a further embodiment, the thin film electrode converter apparatus further includes a third row of holes through the thin film between the first and second rows, and multiple solder connections running from outputs of the ADC through the third row of holes of the thin film to PCB vias.

In a further embodiment, the thin film electrode converter apparatus further includes a surface mount capacitor seated within a hole in the thin film, and solder connections running from end terminations of the surface mount capacitor through to PCB vias.

In a further embodiment, the thin film electrode converter apparatus further comprises an electrostatic discharge (ESD) capacitor connecting between a conductive pad of the thin film and a ground element.

In a further embodiment, the PCB via is a blind via.

In a further embodiment, the solder connection includes gold.

In a further embodiment, the electrodes are biocompatible.

In a further embodiment, the thin film includes two or more layers of embedded wire traces.

In a further embodiment, the thin film through hole is between the first and second rows.

Some embodiments are related to a method of manufacturing a thin film electrode receiving apparatus, the method including providing a thin film having embedded wire traces, the wire traces leading from electrodes at a distal end of the thin film to a two-dimensional (2D) array of conductive pads, wherein some of the wire traces connect with a first row of the conductive pads and other of the wire traces connect with a second row of the conductive pads, the second row being farther from the distal end than the first row, the thin film having a hole through the thin film, sandwiching the thin film between a printed circuit board (PCB) and an analog-to-digital converter (ADC), electrically connecting a first set of ADC inputs with at least one of the first and second rows of conductive pads of the thin film, and heating and forming a solder connection running from an output of the ADC through the thin film hole to the PCB via.

The method can further include attaching an integrated circuit chip to a side of the PCB opposite the thin film and ADC, and connecting the PCB via to the integrated circuit chip.

Some embodiments are related to a method of aligning and joining a thin film flex circuit with a rigid component, the method including depositing, using a ball bonder, a bottom metal ball on a rigid component, stacking, using the ball bonder, another metal ball on top of the bottom metal ball to form a first pillar of stacked metal balls, forming, using the ball bonder, a second pillar of stacked metal balls, and aligning and placing a thin film flex circuit such that the first and second pillars of stacked metal balls project through holes in the thin film flex circuit. The pillars keep the thin film flex circuit taut and prevent wrinkling.

The method can further include bucking each pillar of stacked metal balls projecting through its respective hole to form a buck-tail with a diameter larger than that of the respective hole, thereby riveting the thin film flex circuit to the rigid component.

The pillars can be bucked using a flip chip bonder.

The method can further include drawing, using the ball bonder, a continuous wire between the first and second pillars projecting through the holes, thereby fashioning a staple over the thin film flex circuit onto the rigid component.

The method can further include releasing the thin film flex circuit from a rigid carrier after the aligning and placing.

The rigid component can be an integrated circuit (IC) chip, and the method can further include bonding a ball grid array of the IC chip to exposed pads on the thin film flex circuit.

The thin film flex circuit can be between 5 μm and 20 μm thick, among other thicknesses.

The rigid component can be selected from the group consisting of a printed circuit board (PCB) and an integrated circuit (IC) chip.

The metal balls can include gold, copper, or aluminum, among other materials.

DETAILED DESCRIPTION

Disclosed are a sandwich structure for a thin film electrode array and integrated circuits for use with an implantable brain-computer interface or other sensor interfaces. The electrode array may include wires (also referred to as "threads" or "cables") connected to electrodes implanted in in-vivo neural tissue, such as a brain, and the brain implant system may further include electronics for processing signals from these electrodes, and an electronics enclosure (also referred to as an "electronics package" or a "pillbox") housing containing the electronics. To minimize the volume required by the electronics enclosure housing and/or the brain implant as a whole, the electrode array and integrated circuits can be sandwiched together over a Printed Circuit Board (PCB), and other chips may be located on an opposite side of the PCB. A significant portion of the electrode wire traces and/or connections can be located on a thin film array at a higher density than would be practical on a PCB, thereby further lowering the volume.

In particular, components on one side of the PCB may include chips (e.g., custom application-specific integrated circuits, or ASICs; also referred to as NMICs) and other components used to collect information from the chips. The chips may function as analog-to-digital converters (ADCs) to digitize signals collected from the electrodes, and/or may contain one or more ADCs as components. In addition, the chips may amplify and/or packetize the signals or perform other functions. The terms "chips" and "ADC" may be used interchangeably herein.

On a second side of the PCB, an integrated circuit, such as a field-programmable gate array (FPGA), and other components may be used to aggregate the signals through a single connector. To enable the chips and/or other components above the PCB to communicate with the integrated circuit or FPGA below, the thin-film electrode array on the PCB may contain holes (also referred to as through holes), and the PCB may include vias aligned with the holes, thereby electrically coupling the two sides.

The disclosed apparatus and methods may improve over previous systems by providing such holes and vias, allowing the electronic components to communicate from opposite sides of the PCB, thereby decreasing the volume they occupy. The system also decreases volume by using microfabrication to deposit wire traces at high density on the thin film array. The system provides further improvements by utilizing a connection or fastening strategy of bucking a pillar of stacked gold or other metal balls to rivet a thin film flex circuit. The system can include a thin film having embedded wire traces and holes, a PCB having vias aligned with the holes, sandwiching the thin film, and a solder connection from the chips (which may be referred to as an ADC) through the holes to the vias.

Figure 1:
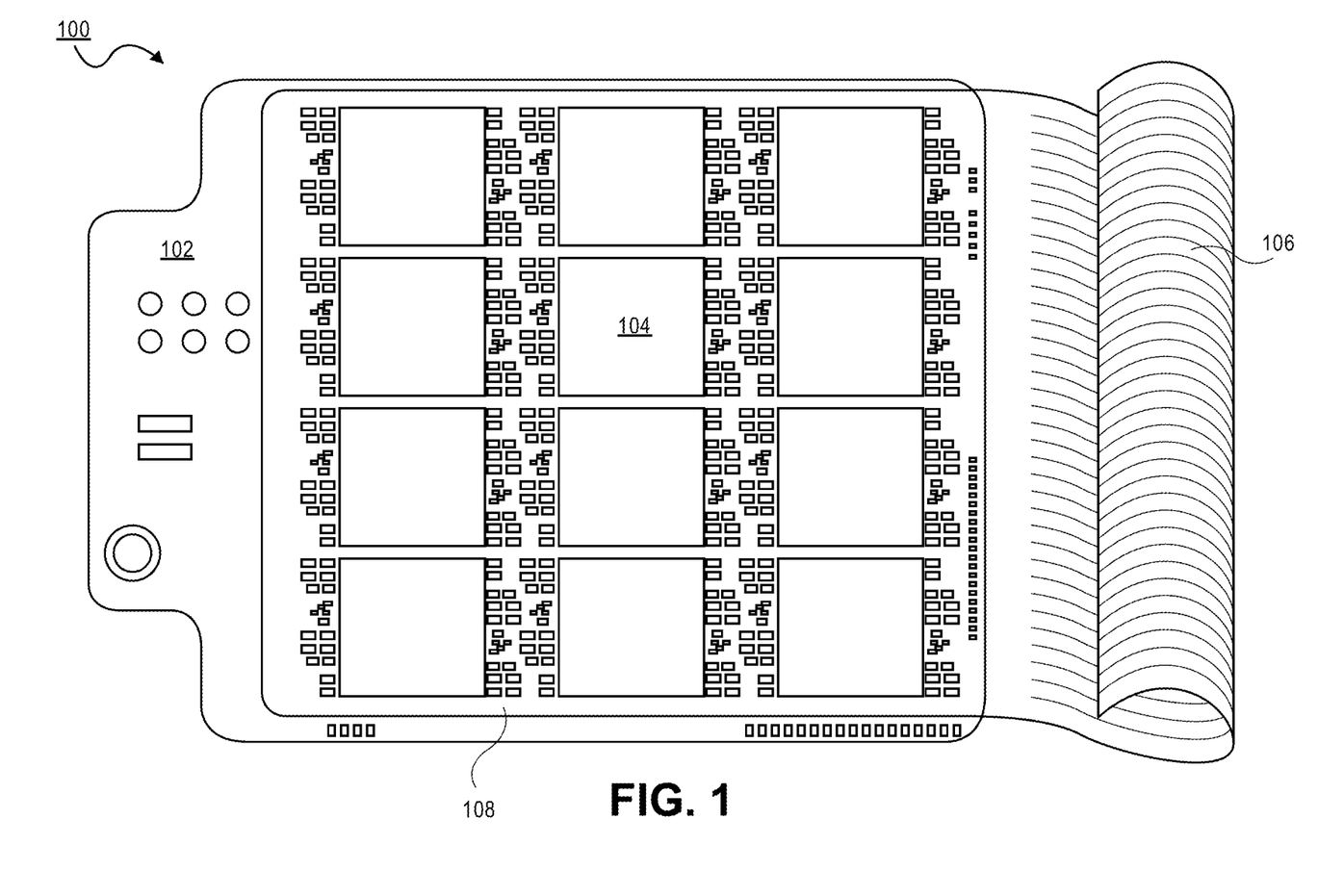
FIG. 1 illustrates a top view of a thin film electrode array on a printed circuit board (PCB), according to embodiments of the present disclosure.

FIG. 1 illustrates components 100 of a brain implant, including a thin film electrode array 108 on a printed circuit board (PCB) 102, according to embodiments of the present disclosure. The thin film electrode array 108 may be part of an electronics package (also referred to as an "electronics enclosure" or a "pillbox") housing electronic components that process signals from the neural tissue. As shown, a thin film electrode array 108 may be situated (or "sandwiched") between PCB 102 and a plurality of chips 104, such as custom ASICs, which may function as ADCs to digitize analog signals received from the electrodes, and/or contain ADCs as components. The chips 104 may further amplify and/or packetize the signals. The chips may be referred to interchangeably as ADCs herein. The thin film electrode array 108 may be less than 50 μm thick, e.g. between 5 μm and 20 μm or other thicknesses as required.

In an embodiment, the thin film electrode array 108 may be microfabricated having electrode wire traces spaced much more closely than would be possible with commercial printing technologies on a PCB, thereby conserving area and/or volume in the electronics package. Beneath the PCB 102, the electronics enclosure may contain an integrated circuit, such as an FPGA, that can aggregate the signals. By situating the chips and FPGA on opposite sides of PCB 102, and by depositing wire traces at high density on the thin film array 108, the disclosed electronics package can occupy less volume, resulting in a smaller, more comfortable, and less obtrusive brain implant.

The thin film array 108 can include contact pads that are electrically coupled to inputs and/or outputs of the chips 104. The thin film array 108 may include, or be coupled to, electrodes, a flex cable, and wires 106, which can stimulate and/or record activity of the neural tissue, e.g., a brain. Wires 106 can be deposited on the thin film array with exceedingly thin diameters, supporting electrodes that are about 20-30 μm in diameter, and can be alternatively referred to as "threads" or "filaments." The PCB may further include cables and/or other connectors.

The thin film array 108 may be made from polymers. Because the thin film array 108 is very thin (e.g., between 5 μm and 20 μm thick), it may be flexible. In some embodiments, stiffening strategies such as van der Waals forces or vacuum pressure, may be used. In some embodiments, using a thicker polymer can stiffen the thin film array 108, even by adding as little as several micrometers in thickness, and can provide sufficient structural strength for the thin film to support the wire traces. Using multiple types of polymer (e.g., two types) in the thin film array can also stiffen the thin film array. Finally, an array attach structure using posts formed from stacked metallic globules and/or staples can fasten the thin film array, as described further below.

In an embodiment, the thin film array 108 can be microfabricated on a silicon wafer. After microfabrication, the thin film can be released from the wafer and attached to a rigid carrier, and the PCB-thin film array-custom chip "sandwich" structure of the electronics enclosure can be assembled. Alternatively, to increase process efficiency and reduce the number of steps, the thin film can remain on the rigid silicon wafer instead of using a carrier. In this case, the thin film 108 remains on the rigid silicon wafer while the electronics package is assembled. The silicon wafer can then be released and etched away after assembling the electronics package.

Figure 2:
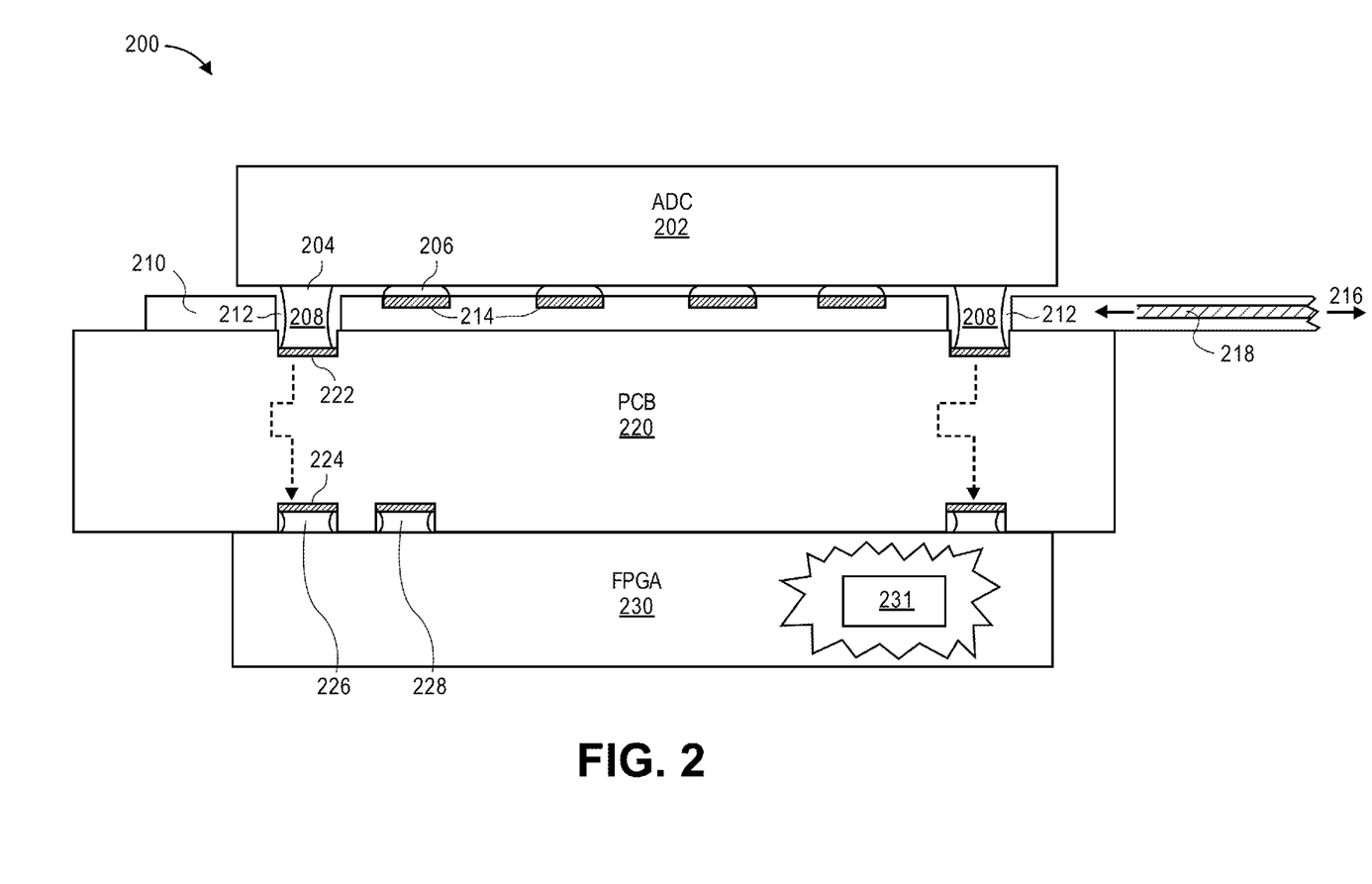
FIG. 2 illustrates a vertical cross-section of electronics package containing a thin film electrode array with holes, aligned with a PCB with vias, according to embodiments of the present disclosure.

FIG. 2 illustrates an electronics package 200 containing a thin film electrode array 210 with holes 212, aligned with a PCB 220 with vias, according to embodiments of the present disclosure. In an embodiment, the holes 212 in thin film electrode array 210 are circular or oval-shaped and measure approximately 95 μm×85 μm. The PCB is approximately rectangular and measure approximately 1.8 cm×2.3 cm. In this example, the holes and vias can electrically couple an ADC 202 above thin film electrode array 210 to an FPGA 230 below PCB 220. In some embodiments, FPGA 230 can be replaced by another type of integrated circuit, and is not limited by the present disclosure.

Proper alignment of the thin film array with the PCB within a tight tolerance, e.g. to within 5 μm or 10 μm over a 20 mm distance, may be important for the proper functioning of the disclosed system. Such precise alignment may be achieved by an array attach structure using posts and/or rivets, as described further below. In some embodiments, the vias can be blind vias.

Contact pads 206 on ADC 202 can electrically couple the wire traces extending from flex cable 218 to ADC 202. Contact pads 206 may be made from solder, and range in size from approximately 50 μm to 100 μm, e.g., 85 μm. In an embodiment, ADC 202 can convert analog electrical signals, received from the neural tissue via electrodes 216, flex cable 218, and wire traces, to digital signals. ADC 202 may also multiplex and/or packetize the signals.

In a typical example, the digital signals output from ADC 202 can transmit from connection point 204 on ADC 202 through hole 212 on solder path 208 to contact pad 222. From contact pad 222, signals can transmit through a via 224 in PCB 220 to the opposite side of PCB 220, and to solder pad 226. From there, the digital signals can be input to FPGA 230, and can be aggregated and/or multiplexed. Thus, electronics package 200 can produce multiple processed signals and can keep track of which custom chip processed each signal.

In some embodiments, FPGA 230 and/or an integrated circuit chip can convert the digital signals to a serialized data structure 231, such as a protocol buffer (i.e., protobuf), Avro, Thrift, Bond, extensible markup language (XML), or another data structure.

The wire traces can be deposited using microfabrication techniques on the thin film electrode array 210, with very close spacing, so that a large number of wires (e.g., 3,000 or 6,000) can be connected to an implant in a limited volume. ADC 202 may comprise a plurality of custom chips, such as custom ASICs, or any other type of ADC, and is not limited by the present disclosure.

Figure 3:
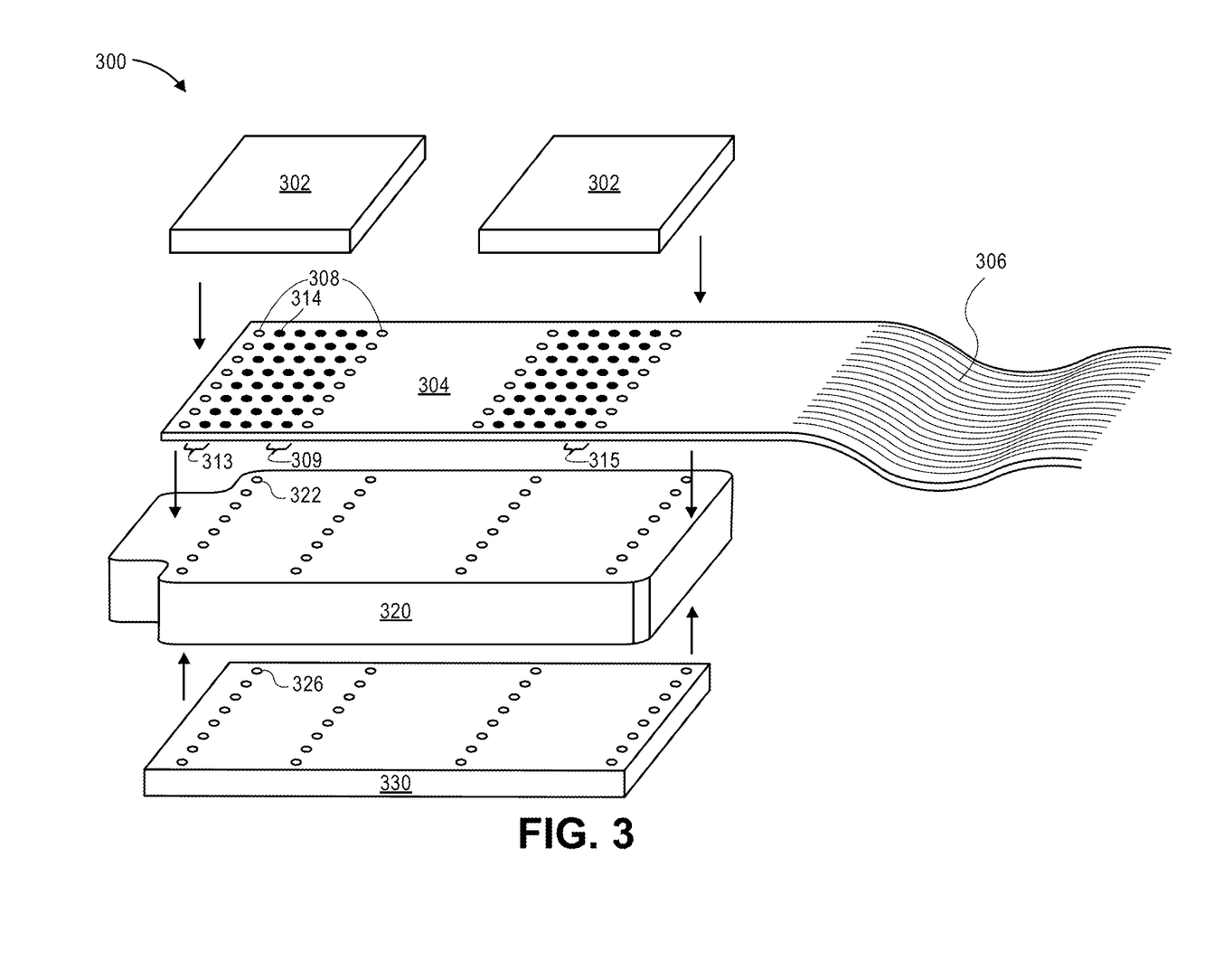
FIG. 3 illustrates an orthogonal projection view of a thin film electrode array with holes on a PCB with vias connecting chips to a field-programmable gate array (FPGA), according to embodiments of the present disclosure.

FIG. 3 illustrates an orthogonal projection view of an electronics package 300 containing chips 302, a thin film electrode array 304 with wires 306 and holes 308, and a PCB 320 with vias 322 connecting chips 302 to a field-programmable gate array (FPGA) 330, according to embodiments of the present disclosure. In some embodiments, some or all of vias 322 can be blind vias.

In this example, electrodes and wires 306 from the electrode continue on the thin film array 304 as wire traces (e.g., several thousand wire traces) leading to contact pads 314. In an embodiment, each wire trace can terminate at its own contact pad. Contact pads 314 may be arranged two-dimensionally, e.g. in rows, on the thin film array 304 to conserve area. In an embodiment, some wire traces can connect with a first row 315 in the array of conductive pads, while other wire traces connect with other respective rows 309 and 313 in the array. In some embodiments, the thin film 304 can include multiple layers of embedded wire traces. In particular, printing wire traces on the thin film 304 at finer pitch, using multiple layers of wire traces, and/or miniaturizing the size of custom chips 302, increases the number of signals that can be input to custom chips 302 for a given volume of electronics package.

In an embodiment, the custom chips 302 (which may also be referred to as NMICs) can receive a plurality of inputs (e.g., 3,000 or 6,000 inputs) from the electrodes, and can multiplex the signals and/or output fewer signals (e.g., on the order of 100 outputs). In a typical example, each custom chip can aggregate a subset of the inputs, e.g. 64 or 256 inputs, into two contact pads, to be transmitted to the FPGA 330. In another example, the chips may be scaled to aggregate larger numbers of inputs and are not limited by the present disclosure. The outputs can be passed to FPGA 330 through holes 308 and vias 322. Thus, FPGA 330 may receive on the order of 100 digital signals, and can aggregate these.

Figure 4:
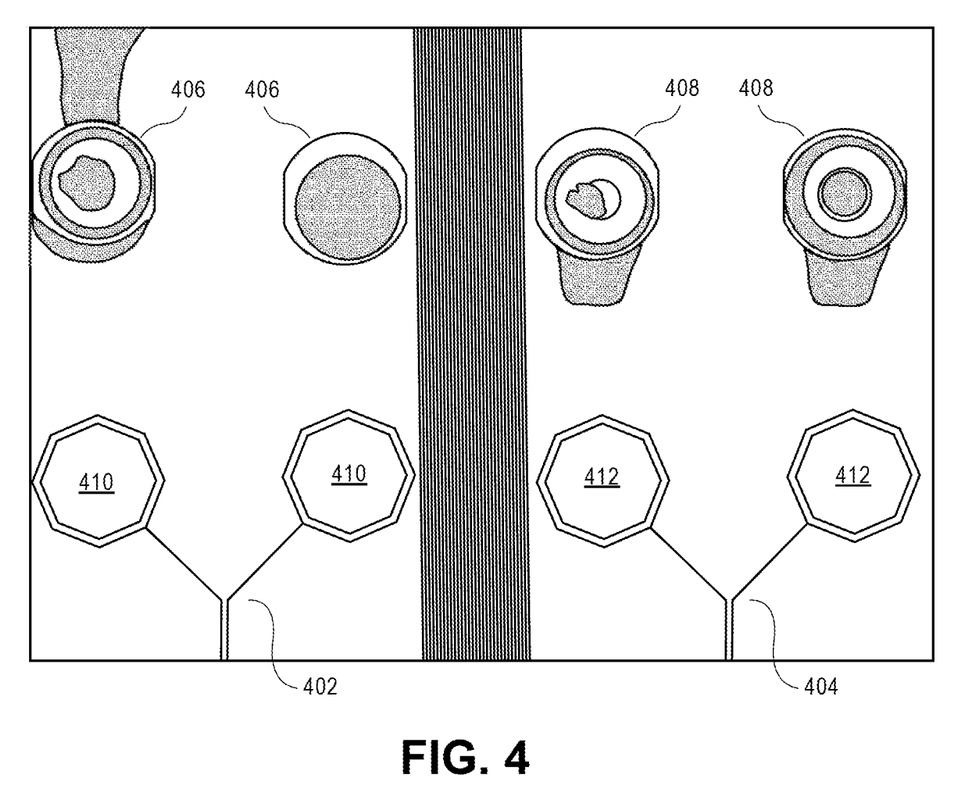
FIG. 4 illustrates a top view of threads and coined contact pads on a thin film electrode array, according to embodiments of the present disclosure.

FIG. 4 illustrates threads 402 and 404 and coined contact pads 406 and 408 on a thin film electrode array, according to embodiments of the present disclosure. In some embodiments, metallic globules, such as gold bumps, can be placed atop the contact pads, such as pads 406 and 408, and can be coined to flatten and level the pads. In this example, the wire traces or threads 402 and 404 terminate at contacts 410 and 412, respectively, which can connect with the custom integrated circuits or chips. The contact pads range in size from approximately 50 µm to 100 µm, e.g., 85 µm, and can be arranged two-dimensionally (e.g., in rows) and/or layered, in order to minimize the volume of the electronics package.

Capacitor Attach

Figure 5:
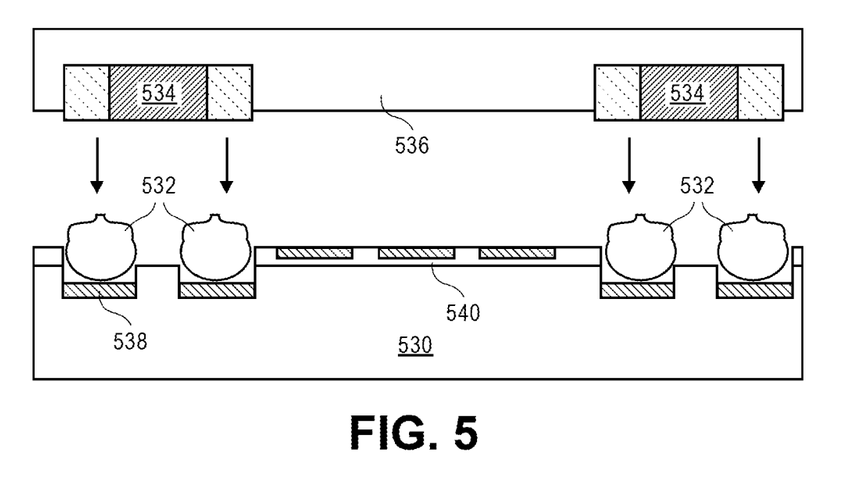
FIG. 5 illustrates a vertical cross section of capacitors attached to an electronics package, according to embodiments of the present disclosure.

FIG. 5 illustrates capacitors 534 attached to an electronics package, according to embodiments of the present disclosure. In some embodiments, in order to minimize the volume of electronics, a plurality of capacitors can be placed above the thin film array 540 (for example, above the chips), and electrically coupled to appropriate points in the electronics package's circuitry. In this case, the capacitors may be electrically coupled to the FPGA using connections through the holes and vias of PCB 530. Alternatively, the capacitors can be fit through the holes in the thin film array 540. In this case, the capacitors may be assembled on the PCB 530 first, and the thin film 540 may then be aligned and fit such that the capacitors fit through the holes. The capacitors can include surface mount capacitors, electrostatic discharge (ESD) capacitors, and/or any type of capacitors, and are not limited by the present disclosure.

The capacitors can be attached by flip-chip bonding. The metallic globules 532 can be microfabricated, and then bonded to interconnect with the capacitors by thermocompression. In an embodiment, this deposition may be performed at a low solder-temperature range, such as between 180° C. and 250° C. The capacitors 534 can be loaded manually in micromachined silicon fixture 536 and attached by flip-chip bonding to the thin film array 540 and/or the custom chips.

In some embodiments, metallic globules 532, e.g. gold bumps or metal balls, can be used to increase the PCB pad or via height, in order to make the metal contact pads the same height. In particular, gold bumps may be used on contact pads 538 that do not make contact with chips. Preventing a height differential between pads with and without contact to chips may improve the overall electrical connection, but may be unnecessary because the thin film array 540 is thin and flexible. The PCB 530 may be recessed by approximately 3 µm to 20 µm, e.g. 15 µm. These recesses can be formed by etching with oxygen plasma, reactive ion etching (RIE), laser, chemical mechanical polishing (CMP)/lapping, or wet etch.

Array Attach

FIGS. 6A-6F illustrate an array attach structure for a thin film electrode array based on rivets made from metallic globules, such as balls or bumps made from gold, copper, or aluminum, and/or solder droplets, according to embodiments of the present disclosure. In various embodiments, posts formed from the metallic globules can hold and align the thin film array on the PCB and can be bucked to form rivets and/or stapled in place. In some embodiments, the pillars can also be used as guide posts without bucking or stapling. The disclosed array attach structure and methods can align the thin film array and PCB with a very tight tolerance, e.g. to within 5 µm or 10 µm over a 20 mm distance. Such accurate alignment can be important for the proper alignment of the wires, contact pads, and electrical connections and the proper functioning of the disclosed system.

Figure 6A:
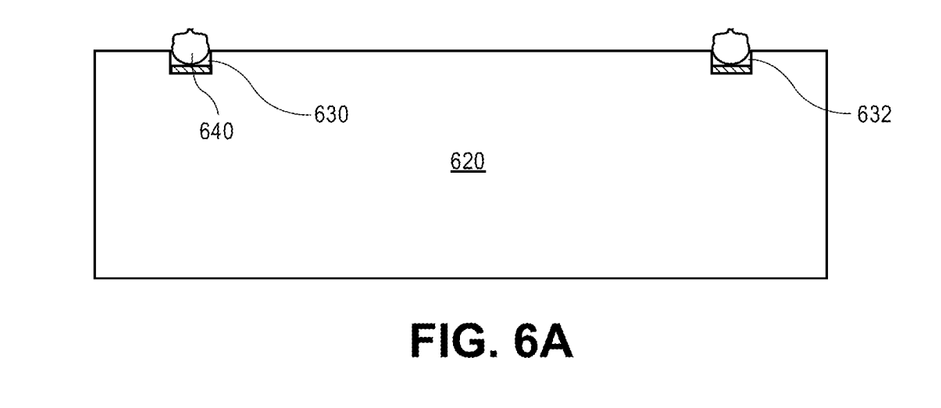
FIG. 6A illustrates a vertical cross section of placing metallic globules for an array attach structure, according to embodiments of the present disclosure.

FIG. 6A illustrates placing metallic globules 640 for an array attach structure, according to embodiments of the present disclosure. In this example, in addition to the vias or through holes for electrical connections, the PCB 620 and/or thin film array can also have holes or recesses 630 and 632 used to hold pillars or posts. These pillars or posts can be used to bond a thin film array (also referred to as a flex component) to PCB 620.

A temporary rigid carrier (e.g., made from silicon or glass) may be used to hold the thin film in place while fastening it to the PCB. In particular, the carrier may hold the thin film while the holes are opened in the thin film. For example, the holes may be mechanically opened using pins.

In the exemplary embodiment, the metallic globules 640 are gold bumps approximately 85 µm in diameter and approximately 60 µm in height. The metallic globules 640 can be deposited with a ball bonder. The globules can be microfabricated and then bonded to interconnect with other components, e.g., using thermocompression. This method may allow more precise deposition compared with solder, and may further avoid chords from solder due to poor metal flow.

Figure 6B:
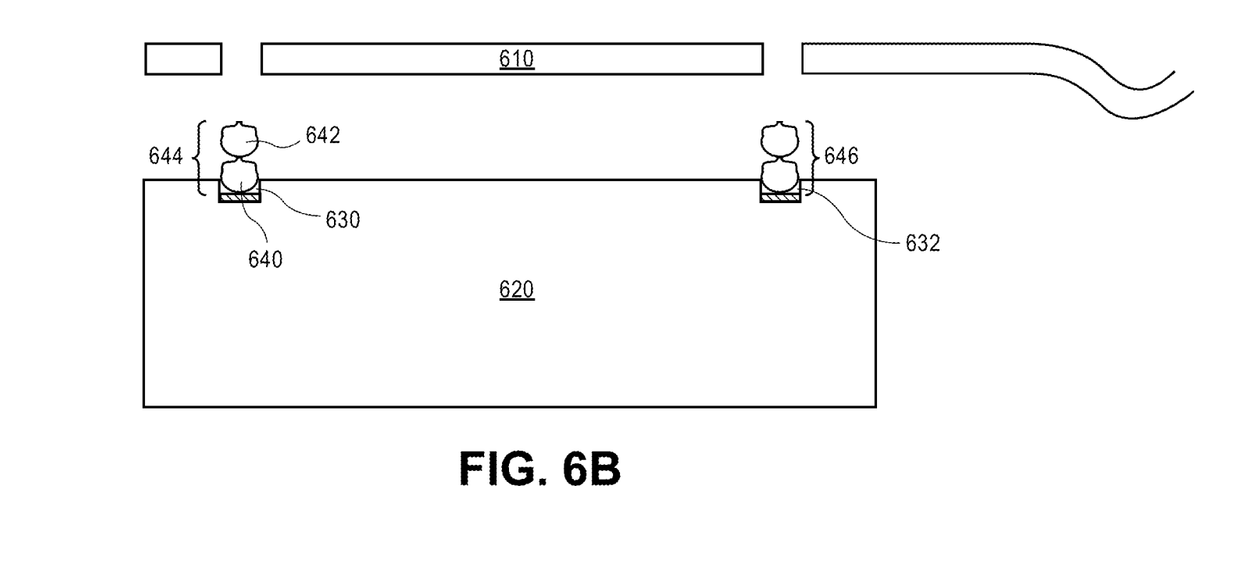
FIG. 6B illustrates stacking metallic globules to form rivet posts for an array attach structure, according to embodiments of the present disclosure.

FIG. 6B illustrates stacking metallic globules to form rivet posts for an array attach structure, according to embodiments of the present disclosure. In this example, a second metallic globule 642 (e.g., gold, copper, or aluminum bumps, and/or solder droplets) is stacked on top of metallic globule 640, for example, using a ball bonder. The metallic globules can be arranged in stacks 644 and 646 (also referred to as pillars or posts) in the holes or recesses 630 and 632 in PBC 620.

A thin film array 610 can be aligned with PBC 620 such that the holes in thin film array 610 line up with the posts and/or the holes 630 and 632 or vias in PBC 620. In an example, the posts can contain two stacked globules each but may also contain another number, and are not limited by the present disclosure.

In some embodiments, the pillars can be formed by depositing (e.g., via a ball bonder or flip chip) metal, such as gold wire, in the hole in thin film 610 and/or PBC 620, moving the ball bonder or flip chip a short distance to shear the metal, and pulling away, thereby creating bumps, droplets, or globules that can be stacked and/or bucked to form a rivet.

Figure 6C:
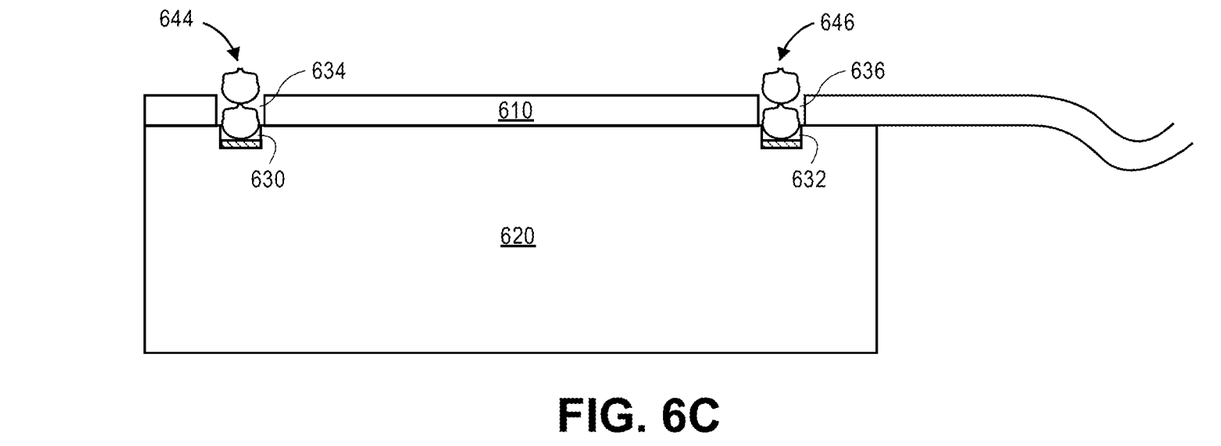
FIG. 6C illustrates assembling an array attach structure, according to embodiments of the present disclosure.

FIG. 6C illustrates assembling an array attach structure, according to embodiments of the present disclosure. As in the example of FIG. 6B, thin film array 610 can be placed on PBC 620 such that the holes 634 and 636 in thin film array 610 align with the posts and/or the holes 630 and 632 or vias in PBC 620. In an embodiment, a temporary rigid carrier can be used to keep thin film array 610 and PBC 620 aligned until they are permanently attached (e.g., by bucking the posts to form rivets, or by stapling).

In some embodiments, aligning thin film array 610 and PBC 620 at a location of a first post and/or inserting a first post through corresponding holes in thin film array 610 and PBC 620 can align thin film array 610 and PBC 620 very precisely. For example, post 644 can first be aligned through hole 634. The first post can then be used as a pivot, while the remaining posts are inserted through the remaining holes in thin film array 610 and PBC 620. In this way, thin film array 610 and PBC 620 can be aligned within a very tight tolerance, e.g. to within 5 µm or 10 µm over a 20 mm distance. In some embodiments, this precise alignment can ensure that the electrodes, wire traces, contact pads, and electronic components align and function correctly.

In some embodiments, the pillars can also be used as guide posts without bucking to form a rivet. The pillars may keep the thin film array 610 taut and prevent wrinkling.

Figure 6D:
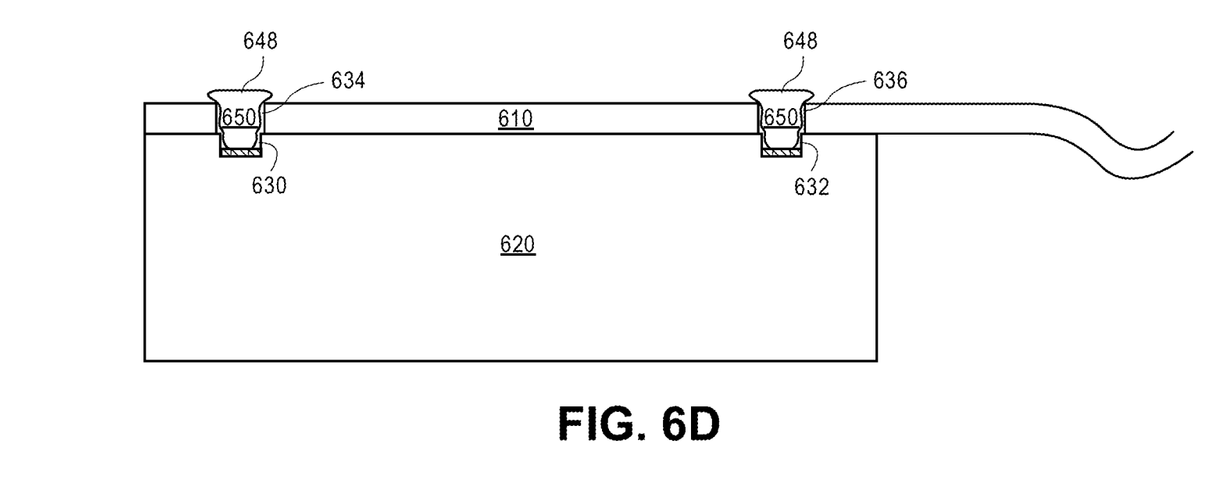
FIG. 6D illustrates bucking stacked metallic globules to form rivets in an array align structure, according to embodiments of the present disclosure.

FIG. 6D illustrates bucking stacked metallic globules to form rivets 650 in an array align structure, according to embodiments of the present disclosure. In some embodiments, a pillar containing a pair of stacked metallic globules can be bucked by mechanical force in order to form rivet structures 650, which can then fasten thin film 610 to the PCB 620. In particular, the pillar can be bucked to form a buck-tail 648 with a diameter larger than that of holes 630-636, thereby riveting the thin film array 610 to the PCB 620.

The pillars may be bucked using a flip chip bonder or ball bonder. The rivets can also keep the thin film flex circuit taut and prevent wrinkling. In some embodiments, instead of two metallic globules, three globules can be stacked to produce a pillar of sufficient height to hold the array in alignment before riveting, and to provide a sufficiently large diameter for the buck-tail to hold the rivet down. In some embodiments, another number of globules, such as four globules, can be stacked, and is not limited by the present disclosure.

The disclosed array attach method can improve over conventional techniques by enabling alignment and bonding at a relatively low temperature. The metallic posts can be bucked by mechanical force to form rivets, thereby avoiding damage to the polymer from heating or curing used in conventional methods, such as bonding methods. In an embodiment, the bucking may be performed at room temperature. With sufficient mechanical pressure, the metallic posts can be sufficiently malleable and thus can attach without the use of adhesive. Alternatively, an elevated melt temperature may also be used, e.g., to physically dissolve the globules.

In an embodiment, the posts can be assembled from the metallic globules and bucked, one at a time. In particular, a first post can be assembled and/or bucked in order to align the thin film and PBC well at the location of the first post, and the first post can then be used as a pivot to align the other sections better. Alternatively, all the posts can be assembled and bucked contemporaneously. After bucking the posts, a rigid carrier may be removed from the electronics package assembly.

Figure 6E:
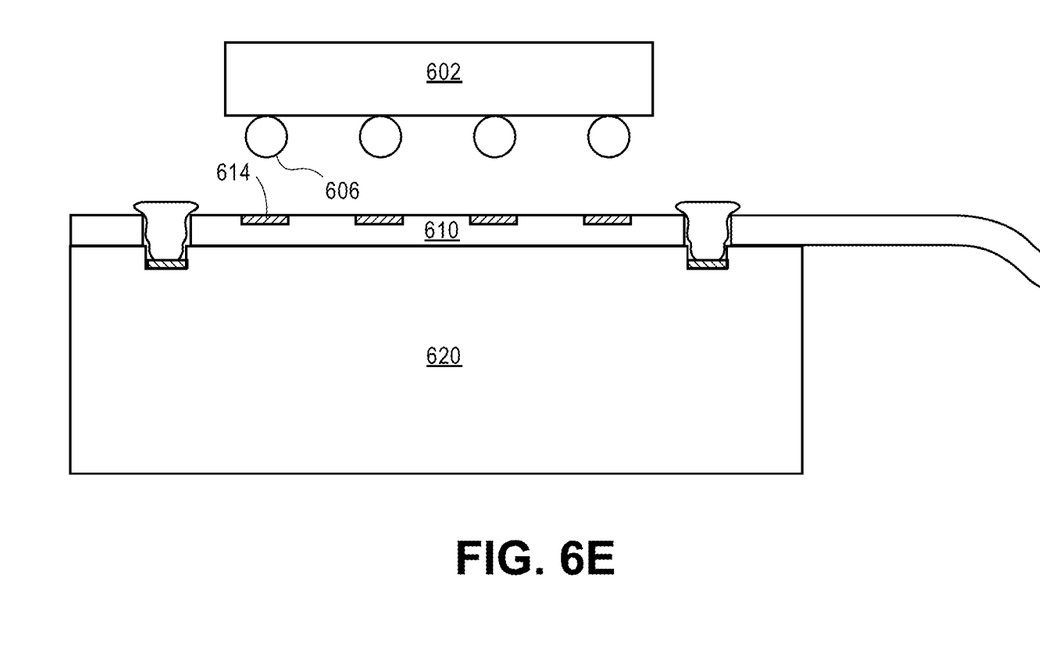
FIG. 6E illustrates assembling an electronics package including an array align structure, according to embodiments of the present disclosure.

FIG. 6E illustrates assembling an electronics package including an array align structure, according to embodiments of the present disclosure. In this example, once thin film array 610 and PCB 620 have been riveted together by bucking the posts, integrated circuit or chip 602 can be placed on thin film array 610, to form the main sandwich assembly of the electronics package. Chip 602 can make electrical contact with contact pads 614. In some embodiments, chip 602 can be electrically coupled to contact pads 614 by solder balls 606.

In particular, the chip 602 can be one of a plurality of custom chips (also referred to as NMICs) with solder balls 606 pre-attached. In an embodiment, solder balls 606 can be approximately 80 µm to 100 µm in diameter and approximately 60 µm in height. Solder balls 606 can pass through a hole in thin film electrode array 610 and can bond to PCB 620 underneath. Because thin film electrode array 610 is very thin (e.g., 5 µm to 20 µm), solder balls 606 are sufficiently large to pass through holes and electrically couple the chip 602 to the vias of PCB 620, an FPGA, and/or other components. The disclosed system and methods thereby improve over conventional systems that must use conductive fill. Furthermore, because thin film electrode array 610 is thin, it may be unnecessary to use different sized solder balls.

Figure 6F:
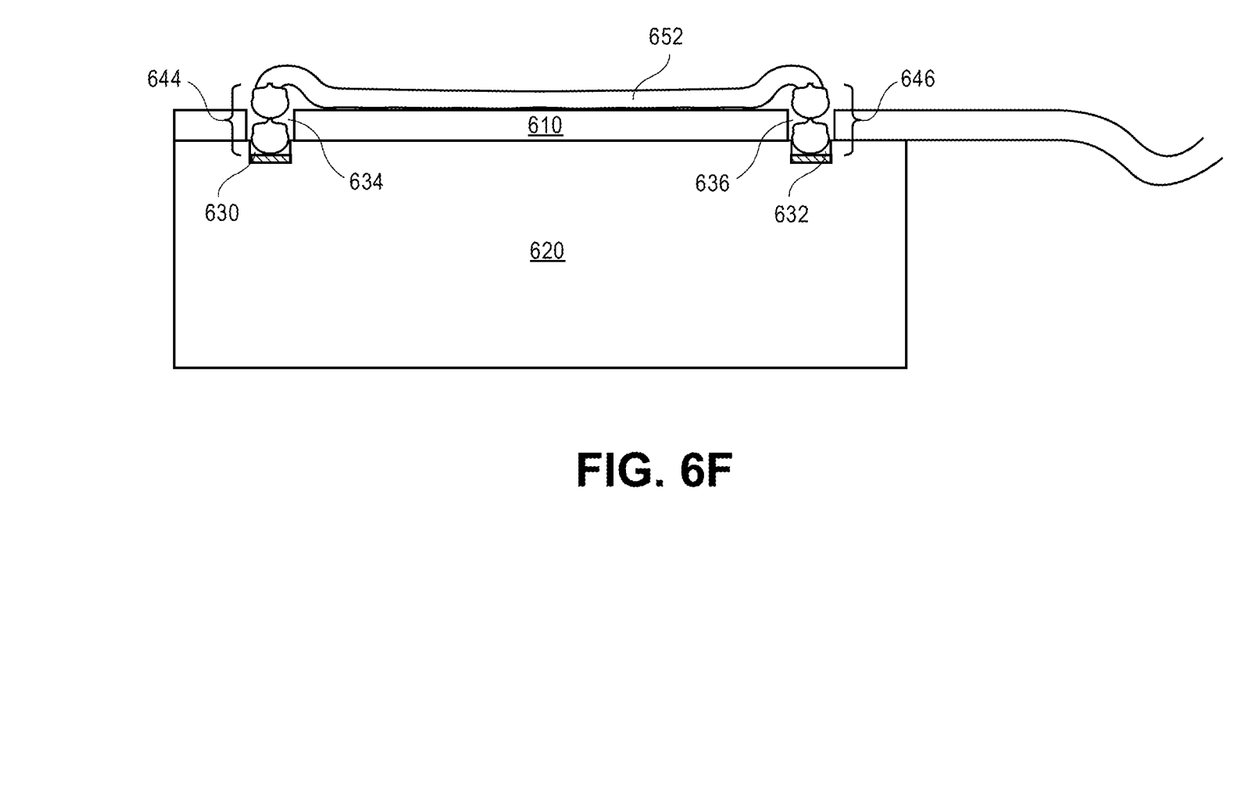
FIG. 6F illustrates stapling a thin film with stacked metallic globules for an array staple structure, according to embodiments of the present disclosure.

FIG. 6F illustrates stapling a thin film with stacked metallic globules for an array staple structure, according to embodiments of the present disclosure. In some embodiments, the staple 652 can be made from gold wire or aluminum wire. In an embodiment, the staple 652 can be inserted into holes 634 and 636 in thin film array 610 and/or holes 630 and 632 in PCB 620. Staple 652 can also be joined to stacked metallic globules 644 and 646, e.g., gold bumps or aluminum or copper balls. In an embodiment, the staple can be formed as a wire, e.g., by pulling off a ball bonder while depositing the metal into a hole (e.g., holes 630 and 634), pulling the ball bonder up gently, and depositing metal into the next hole (e.g., holes 632 and 636). The globules can be formed using a similar technique, but shearing the metal to form a globule, rather than pulling off.

The posts or stacked metallic globules 644 and 646 can be used together with staple 652 to enable precision alignment. Alternatively, in particular for an application where the electronics package is larger and/or a higher alignment tolerance is viable, the staple can be deposited without posts.

Figure 7:
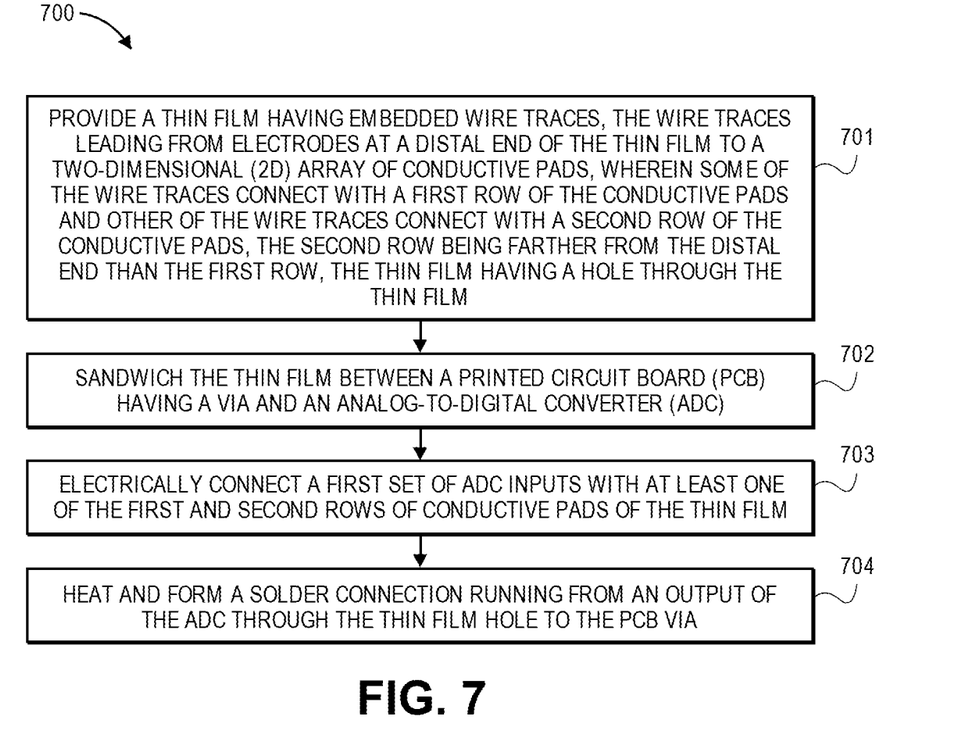
FIG. 7 is a flowchart illustrating an embodiment in accordance with the present invention.

FIG. 7 is a flowchart of a process 700 in accordance with an embodiment. In operation 701, a thin film having embedded wire traces is provided. The wire traces lead from electrodes at a distal end of the thin film to a two-dimensional (2D) array of conductive pads, where some of the wire traces connect with a first row of the conductive pads and other of the wire traces connect with a second row of the conductive pads, the second row being farther from the distal end than the first row, the thin film having a hold therethrough. In operation 702, the thin film is sandwiched between a printed circuit board (PCB) having a via and an analog-to-digital converter (ADC). In operation 703, a first set of ADC inputs are electrically connected with at least one of the first and second rows of conductive pads of the thin film. In operation 704, a solder connection running from an output of the ADC through the thin film hole to the PCB via is heated and formed.

Figure 8:
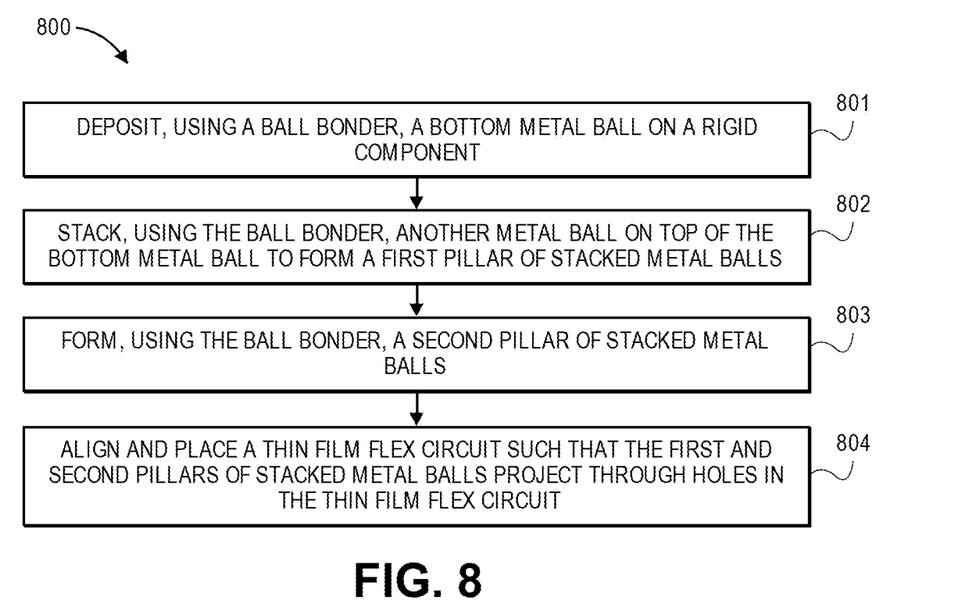
FIG. 8 is a flowchart illustrating an embodiment in accordance with the present invention.

FIG. 8 is a flowchart of a process 800 in accordance with an embodiment. In operation 801, a bottom metal ball is deposited on a rigid component using a ball bonder. In operation 802, another metal ball is stacked on top of the bottom metal ball to form a first pillar of stacked metal balls. In operation 803, a second pillar of stacked metal balls is formed using the ball bonder. In operation 804, a thin film flex circuit is aligned and placed such that the first and second pillars of stacked metal balls project through holes in the thin film flex circuit.

It should be appreciated that a brain implant or other system and a respective control system for the brain implant can have one or more microprocessors/processing devices that can further be a component of the overall apparatuses. The control systems are generally proximate to their respective devices, in electronic communication (wired or wireless) and can also include a display interface and/or operational controls configured to be handled by a user to monitor the respective systems, to change configurations of the respective systems, and to operate, directly guide, or set programmed instructions for the respective systems, and sub-portions thereof. Such processing devices can be communicatively coupled to a non-volatile memory device via a bus. The non-volatile memory device may include any type of memory device that retains stored information when powered off. Non-limiting examples of the memory device include electrically erasable programmable read-only memory ("ROM"), flash memory, or any other type of non-volatile memory. In some aspects, at least some of the memory device can include a non-transitory medium or memory device from which the processing device can read instructions. A non-transitory computer-readable medium can include electronic, optical, magnetic, or other storage devices capable of providing the processing device with computer-readable instructions or other program code. Non-limiting examples of a non-transitory computer-readable medium include (but are not limited to) magnetic disk(s), memory chip(s), ROM, random-access memory ("RAM"), an ASIC, a configured processor, optical storage, and/or any other medium from which a computer processor can read instructions. The instructions may include processor-specific instructions generated by a compiler and/or an interpreter from code written in any suitable computer-programming language, including, for example, C, C++, C#, Java, Python, Perl, JavaScript, etc.

While the above description describes various embodiments of the invention and the best mode contemplated, regardless how detailed the above text, the invention can be practiced in many ways. Details of the system may vary considerably in its specific implementation, while still being encompassed by the present disclosure. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

In some embodiments, the systems and methods of the present disclosure can be used in connection with neurosurgical techniques. However, one skilled in the art would recognize that neurosurgical techniques are a non-limiting application, and the systems and methods of the present disclosure can be used in connection with any biological tissue. Biological tissue can include, but is not limited to, the brain, muscle, liver, pancreas, spleen, kidney, bladder, intestine, heart, stomach, skin, colon, and the like.

The systems and methods of the present disclosure can be used on any suitable multicellular organism including, but not limited to, invertebrates, vertebrates, fish, bird, mammals, rodents (e.g., mice, rats), ungulates, cows, sheep, pigs, horses, non-human primates, and humans. Moreover, biological tissue can be ex vivo (e.g., tissue explant), or in vivo (e.g., the method is a surgical procedure performed on a patient).

The teachings of the invention provided herein can be applied to other systems, not necessarily the system described above. The elements and acts of the various examples described above can be combined to provide further implementations of the invention. Some alternative implementations of the invention may include not only additional elements to those implementations noted above, but also may include fewer elements. Further any specific numbers noted herein are only examples; alternative implementations may employ differing values or ranges, and can accommodate various increments and gradients of values within and at the boundaries of such ranges.

References throughout the foregoing description to features, advantages, or similar language do not imply that all of the features and advantages that may be realized with the present technology should be or are in any single embodiment of the invention. Rather, language referring to the features and advantages is understood to mean that a specific feature, advantage, or characteristic described in connection with an embodiment is included in at least one embodiment of the present technology. Thus, discussion of the features and advantages, and similar language, throughout this specification may, but do not necessarily, refer to the same embodiment. Furthermore, the described features, advantages, and characteristics of the present technology may be combined in any suitable manner in one or more embodiments. One skilled in the relevant art will recognize that the present technology can be practiced without one or more of the specific features or advantages of a particular embodiment. In other instances, additional features and advantages may be recognized in certain embodiments that may not be present in all embodiments of the present technology.

What is claimed is:

1. A thin film electrode converter apparatus comprising:
a thin film having embedded wire traces, the wire traces leading from electrodes at a flexible distal end of the thin film to a two-dimensional (2D) array of conductive pads, wherein some of the wire traces connect with a first row of the conductive pads and other of the wire traces connect with a second row of the conductive pads, the second row being farther from the distal end than the first row, the thin film having a hole through the thin film;
a printed circuit board (PCB) having a via aligned with the hole through the thin film;
an analog-to-digital converter (ADC) sandwiching the thin film between the ADC and the PCB and having ADC inputs electrically connected with at least one of the first and second rows of conductive pads of the thin film; and a solder connection running from an output of the ADC through the thin film hole to the PCB via.

2. The apparatus of claim 1 further comprising:
an integrated circuit chip attached to a side of the PCB opposite the thin film and ADC, the integrated circuit chip connected with the PCB via.

3. The apparatus of claim 2 wherein the integrated circuit chip comprises a field programmable gate array (FPGA).

4. The apparatus of claim 2 wherein:
the ADC is configured to convert analog signals from multiple electrodes into digital signals and multiplex them together;
the solder connection is configured to route the multiplexed digital signal from the ADC on one side of the thin film to the integrated circuit chip on another side; and
the integrated circuit chip is configured to convert the multiplexed digital signals to a serialized data structure.

5. The apparatus of claim 4 wherein the serialized data structure is in a format selected from the group consisting of Protocol Buffers, Avro, Thrift, Bond, and extensible markup language (XML).

6. The apparatus of claim 1 wherein the ADC is configured to multiplex multiple digital signals together.

7. The apparatus of claim 1 wherein each conductive pad of the thin film is at least 5 times wider than its respective wire trace.

8. The apparatus of claim 1 further comprising:
a third row of holes through the thin film between the first and second rows; and
multiple solder connections running from outputs of the ADC through the third row of holes of the thin film to PCB vias.

9. The apparatus of claim 1 further comprising:
a surface mount capacitor seated within a hole in the thin film; and
solder connections running from end terminations of the surface mount capacitor through to PCB vias.

10. The apparatus of claim 1 further comprising:
an electrostatic discharge (ESD) capacitor connecting between a conductive pad of the thin film and a ground element.

11. The apparatus of claim 1 wherein the PCB via is a blind via.

12. The apparatus of claim 1 wherein the solder connection includes gold.

13. The apparatus of claim 1 wherein the electrodes are biocompatible.

14. The apparatus of claim 1 wherein the thin film includes two or more layers of embedded wire traces.

15. The apparatus of claim 1 wherein the thin film through hole is between the first and second rows.

16. A method of manufacturing a thin film electrode receiving apparatus, the method comprising:
providing a thin film having embedded wire traces, the wire traces leading from electrodes at a distal end of the thin film to a two-dimensional (2D) array of conductive pads, wherein some of the wire traces connect with a first row of the conductive pads and other of the wire traces connect with a second row of the conductive pads, the second row being farther from the distal end than the first row, the thin film having a hole through the thin film;
sandwiching the thin film between a printed circuit board (PCB) having a via and an analog-to-digital converter (ADC);
electrically connecting a first set of ADC inputs with at least one of the first and second rows of conductive pads of the thin film;
heating and forming a solder connection running from an output of the ADC through the thin film hole to the PCB via;
attaching an integrated circuit chip to a side of the PCB opposite the thin film and ADC; and
connecting the PCB via to the integrated circuit chip.

17. A method of aligning and joining a thin film flex circuit with a rigid component, the method comprising:
depositing, using a ball bonder, a bottom metal ball on a rigid component;
stacking, using the ball bonder, another metal ball on top of the bottom metal ball to form a first pillar of stacked metal balls;
forming, using the ball bonder, a second pillar of stacked metal balls; and
aligning and placing a thin film flex circuit such that the first and second pillars of stacked metal balls project through holes in the thin film flex circuit;
wherein the pillars keep the thin film flex circuit taut and prevent wrinkling.

18. The method of claim 17 further comprising:
bucking each pillar of stacked metal balls projecting through its respective hole to form a buck-tail with a diameter larger than that of the respective hole, thereby riveting the thin film flex circuit to the rigid component.

19. The method of claim 18 wherein the pillars are bucked using a flip chip bonder.

20. The method of claim 17 further comprising:
drawing, using the ball bonder, a continuous wire between the first and second pillars projecting through the holes, thereby fashioning a staple over the thin film flex circuit onto the rigid component.

21. The method of claim 17 further comprising:
releasing the thin film flex circuit from a rigid carrier after the aligning and placing.

22. The method of claim 17 wherein the rigid component is an integrated circuit (IC) chip, the method further comprising:
bonding a ball grid array of the IC chip to exposed pads on the thin film flex circuit.

23. The method of claim 17 wherein the thin film flex circuit is between 5 µm and 20 µm thick.

24. The method of claim 17 wherein the rigid component is selected from the group consisting of a printed circuit board (PCB) and an integrated circuit (IC) chip.

25. The method of claim 17 wherein the metal balls comprise gold, copper, or aluminum.

* * * * *